(12) United States Patent
Geitz

(10) Patent No.: US 6,551,278 B1
(45) Date of Patent: Apr. 22, 2003

(54) MINIATURE X-RAY CATHETER WITH RETRACTABLE NEEDLES OR SUCTION MEANS FOR POSITIONING AT A DESIRED SITE

(75) Inventor: Kurt Alfred Edward Geitz, Sudbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 82 days.

(21) Appl. No.: 09/709,669

(22) Filed: Nov. 10, 2000

(51) Int. Cl.$^7$ .................. A61M 37/00; A61M 5/78; A61M 5/20; A61B 18/18

(52) U.S. Cl. ............... 604/131; 604/164.01; 604/156; 604/103.03; 606/2

(58) Field of Search ............... 607/129, 88; 378/64, 378/119, 121, 145, 130, 219, 110, 205; 600/143, 3, 1, 2, 463; 604/164.01, 164.07, 131, 171; 345/67; 250/493.1; 372/5; 606/3, 15, 17

(56) References Cited

U.S. PATENT DOCUMENTS

| | | | |
|---|---|---|---|
| 3,811,426 A | * 5/1974 | Culver et al. | ........... 250/493.1 |
| 4,143,275 A | * 3/1979 | Mallozzi et al. | ........... 372/5 |
| 4,641,649 A | 2/1987 | Walinsky et al. | |
| 4,652,846 A | 3/1987 | Sobottka | |
| 4,860,744 A | 8/1989 | Johnson et al. | |
| 4,993,404 A | 2/1991 | Lane | |
| 5,006,119 A | 4/1991 | Acker et al. | |
| 5,041,107 A | 8/1991 | Heil, Jr. | |
| 5,084,061 A | 1/1992 | Gau et al. | |
| 5,127,394 A | 7/1992 | Lane | |
| 5,151,100 A | 9/1992 | Abele et al. | |
| 5,153,900 A | * 10/1992 | Nomikos et al. | ........... 378/110 |
| 5,165,093 A | * 11/1992 | Miller et al. | ............ 378/130 |
| 5,230,349 A | 7/1993 | Langberg | |

(List continued on next page.)

FOREIGN PATENT DOCUMENTS

| | | |
|---|---|---|
| CA | WO 98/48899 | * 11/1998 |
| WO | 97/07740 | 3/1997 |
| WO | 98/48899 | 11/1998 |
| WO | 00/09212 | 2/2000 |

OTHER PUBLICATIONS

Gutman et al, X–ray system with implantable neelde for treatment of cancer, U.S Patent Application Publication No. 2002/003856, Jan. 10, 2002.*

Amano et al, Plasma–Or Serum–Collecting Device, U.S Patent Publication Application No. 2001/0045387, Nov. 29, 2001.*

Chornecndy et al, X–Ray Catheter, U.S Patent Publication Application No. 2001/0009970, Jul. 26, 2001.*

*Primary Examiner*—Michael J. Hayes
*Assistant Examiner*—Roz Ghafoorian
(74) *Attorney, Agent, or Firm*—Fulbright & Jaworski L.L.P.

(57) ABSTRACT

An x-ray catheter has an x-ray tube having an x-ray source therein and an x-ray transparent window through which x-rays may pass is positioned with retractable needles or suction. The needles, if present, are retractably attached to a hinge which is operatively connected to a control that extends or retracts the needles from the device, the needles positioned adjacent the x-ray transparent window so as not to impede the flow of x-rays. Alternatively, suction opening operatively connected to a vacuum source positions the x-ray source at the desired site.

9 Claims, 4 Drawing Sheets

U.S. PATENT DOCUMENTS

| | | | |
|---|---|---|---|
| 5,354,220 A | | 10/1994 | Ganguly et al. |
| 5,369,679 A | * | 11/1994 | Sliski et al. ................. 378/205 |
| 5,372,603 A | | 12/1994 | Acker et al. |
| 5,422,926 A | * | 6/1995 | Smith et al. ................. 378/121 |
| 5,442,678 A | * | 8/1995 | Dinsmore et al. .......... 378/119 |
| 5,528,652 A | * | 6/1996 | Smith et al. ................. 378/108 |
| 5,542,928 A | | 8/1996 | Evans et al. |
| 5,562,633 A | | 10/1996 | Wozencroft |
| 5,566,221 A | * | 10/1996 | Smith et al. ................. 378/145 |
| 5,591,162 A | | 1/1997 | Fletcher et al. |
| 5,599,346 A | | 2/1997 | Edwards et al. |
| 5,621,780 A | * | 4/1997 | Smith et al. ................. 378/119 |
| 5,651,047 A | * | 7/1997 | Moorman et al. ............ 378/19 |
| 5,704,914 A | * | 1/1998 | Stocking et al. ....... 604/164.07 |
| 5,718,688 A | | 2/1998 | Wozendroft |
| 5,782,740 A | | 7/1998 | Schneiderman |
| 5,793,272 A | | 8/1998 | Burghartz et al. |
| 5,795,339 A | * | 8/1998 | Erskine ...................... 604/171 |
| 5,816,999 A | | 10/1998 | Bischoff et al. |
| 5,865,806 A | | 2/1999 | Howell |
| 5,919,172 A | * | 7/1999 | Golba, Jr. .............. 604/164.01 |
| 5,997,462 A | * | 12/1999 | Loffler ........................... 600/3 |
| 6,095,966 A | * | 8/2000 | Chornenky et al. ............ 600/3 |
| 6,143,018 A | * | 11/2000 | Beuthan et al. ............... 604/20 |
| 6,171,249 B1 | * | 1/2001 | Chin et al. .................. 600/143 |
| 6,190,359 B1 | * | 2/2001 | Heruth ....................... 604/131 |
| 6,217,503 B1 | * | 4/2001 | Weinberger et al. ............ 600/1 |
| 6,251,060 B1 | * | 6/2001 | Hooft et al. .................... 600/3 |
| 6,301,328 B1 | * | 10/2001 | Sliski et al. .................. 378/64 |
| 6,330,481 B1 | * | 12/2001 | Van Wijk et al. ........... 607/129 |
| 6,364,840 B1 | * | 4/2002 | Crowley ..................... 600/463 |
| 6,375,651 B2 | * | 4/2002 | Grasso et al. ................. 606/15 |

* cited by examiner

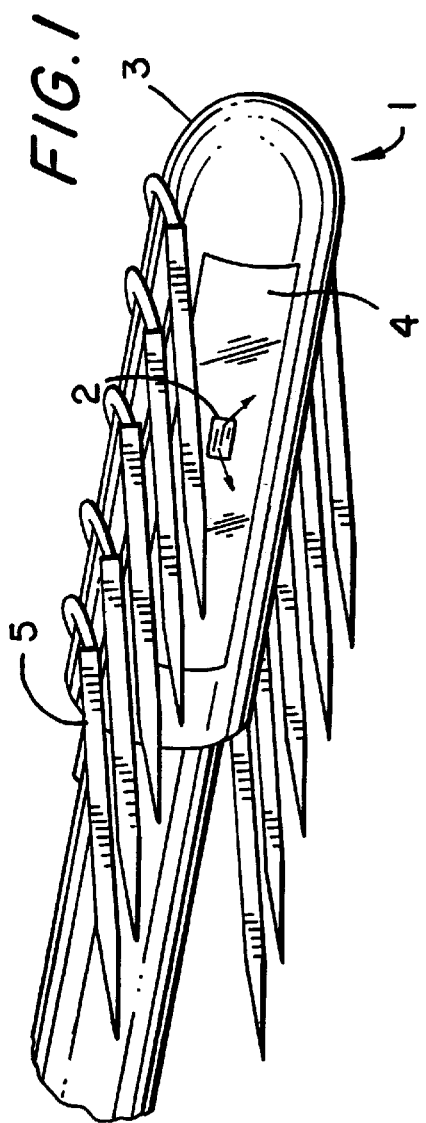
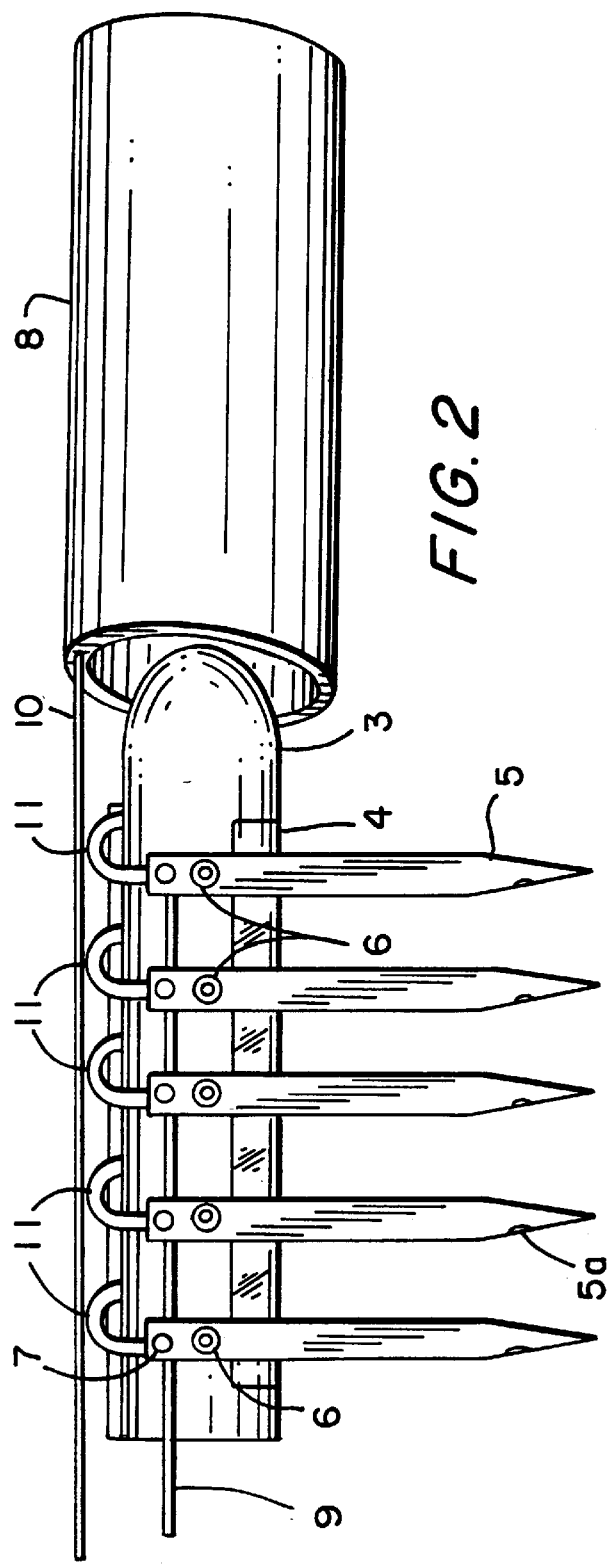

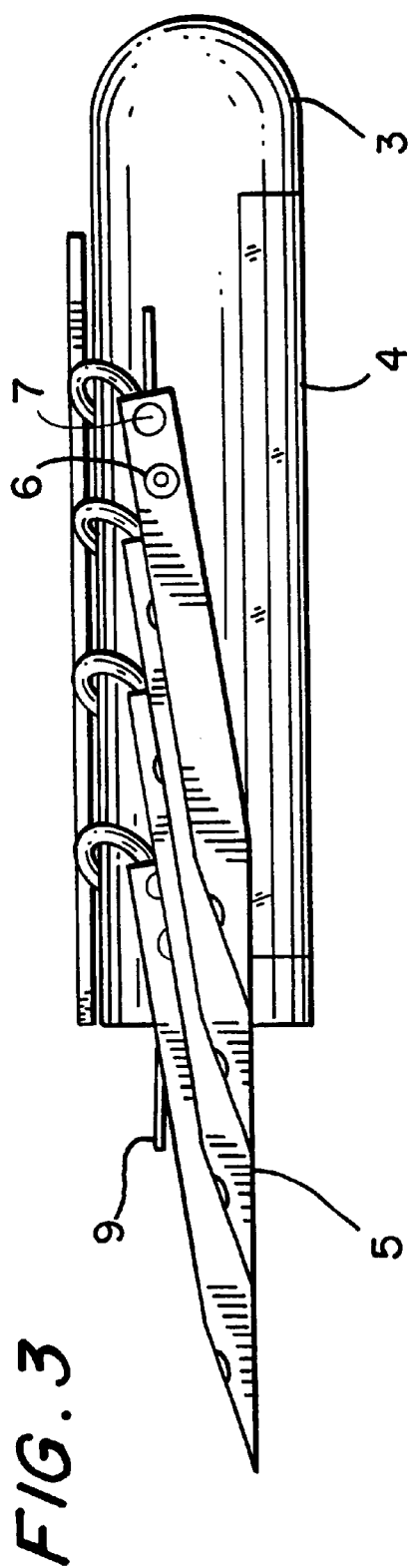
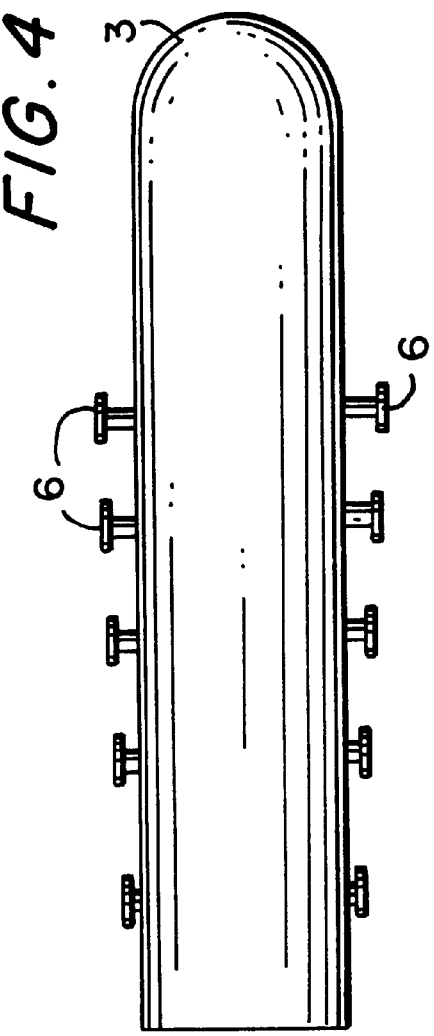

MINIATURE X-RAY CATHETER WITH RETRACTABLE NEEDLES OR SUCTION MEANS FOR POSITIONING AT A DESIRED SITE

FIELD OF THE INVENTION

The invention relates to a miniaturized x-ray having a x-ray source catheter that generates x-rays while minimizing risk of exposure to the x-rays. Retractable needles are provided to anchor the x-ray source at a desired site or to deliver therapeutic or diagnostic agents.

BACKGROUND OF THE INVENTION

Traditionally, x-rays have been used in the medical industry to view bone, tissue and teeth. X-rays have also been used to treat cancerous and precancerous conditions by exposing a patient to x-rays using an external x-ray source. Treatment of cancer with x-rays presents many well documented side effects, many of which are due to the broad exposure of the patient to the therapeutic x-rays.

Minimally invasive endoscopic techniques have been developed and are used to treat a variety of conditions. Endoluminal procedures are procedures performed with an endoscope, a tubular device into a lumen of which may be inserted a variety of rigid or flexible tools to treat or diagnose a patient's condition. Endoscopes can be either rigid or flexible, and are chosen according to the desired application.

The desire for improved minimally invasive medical devices and techniques have led to the development of miniaturized x-ray devices that may be used in the treatment or prevention of a variety of medical conditions. International Publication No. WO 98/48899 describes a miniature x-ray unit having an anode and cathode separated by a vacuum gap positioned inside a metal housing. The anode includes abase portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 describes an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

U.S. Pat. No. 5,795,339 describes a catheter-advancement actuated needle retraction system is disclosed herein. The invention includes a generally hollow barrel that houses a needle hub, which can include a flashback chamber. A needle is affixed to the distal end of the needle hub and is aligned to extend through an opening in the distal end of the barrel. The needle extends through a catheter hub and catheter affixed to the catheter hub. A spring is disposed in the barrel lumen to cooperate with the needle hub to urge the needle hub toward the proximal end of the barrel. A latch actuator is releasably engaged with the catheter hub. A latch, which cooperates with the latch actuator, is movable between one position, which maintains the needle hub adjacent to the distal end of the barrel, and a second position allowing the spring to urge the needle hub to the proximal end of the barrel. A mechanism may be provided to cushion the needle hub as it contacts the proximal end of the barrel by the force of the spring.

U.S. Pat. No. 5,865,806 describes a one step catheter advancement automatic needle retraction system. It comprises a generally hollow barrel, a needle hub which can include a flashback chamber disposed in the barrel, a secondary flashback chamber disposed in the barrel, a biasing mechanism for retracting the needle into the barrel and a clip associated with the secondary flashback chamber for engaging a catheter hub. The needle hub in conjunction with the secondary flashback chamber retains the needle in the extended position against the force of the biasing mechanism until the catheter has been advanced a certain distance from the distal end of the barrel.

U. S. Pat. No. 5,718,688 describes a catheter placement unit comprising a catheter having an axial bore, a catheter hub at one end of the catheter, an introducing needle having a pointed tip for introducing the catheter into a desired position in a patient's body, and a needle hub on the needle remote from the tip for mounting the needle so that it extends through the catheter bore for introduction of the catheter into the patient's body and so that it can subsequently be withdrawn from the catheter bore leaving the catheter in position in the patient's body. The unit includes a needle tip protector on the needle for shielding the needle tip when the needle has been withdrawn from the catheter bore. The needle tip protector includes a locking device which is initially in an unlocked position permitting withdrawal of the needle from the catheter bore but which is arranged to be placed in a locked position, in which the locking device engages the outer surface of the needle, by withdrawal of the needle from the catheter bore so as to lock the needle tip protector on the needle in the shielding position. The locking device retains the catheter hub on the needle when the locking device is in the unlocked position and releases the catheter hub from the needle when the locking device is in the locked position. Separation of the catheter from the needle is therefore prevented until the needle has been drawn from the catheter bore to trigger shielding of the needle tip.

U.S. Pat. No. 5,704,914 describes a catheter assembly is which includes a flexible catheter, a hub attached to the catheter which defines a lumen and an adjoining flash back chamber which communicate with the catheter, and a flexible resilient diaphragm attached to the hub through which a hypodermic needle such as a catheter introducer needle can be passed. The diaphragm prevents a liquid, such as blood, which has been introduced into the hub lumen from flowing past the diaphragm and beyond the hub when the diaphragm is unpenetrated. A hollow tubular body may also be included to which a cannulated catheter needle can be either stationarily or movably attached. The body is removably attached to the hub behind the diaphragm. If movably attached to the body, the needle has a retracted position fully recessed within the body for safe storage and an advanced operative position extending through the diaphragm, hub and catheter. A needle occluding member may also be provided to prevent a liquid such as blood from flowing through the needle into the body. The member may be a movable guide wire or a stationary obturator member. A liquid outlet port can be provided on the side of the hub and a multi-position stop cock can be mounted on the hub to direct liquid flow from the catheter to the side port while blocking flow toward the diaphragm and vise versa.

U.S. Pat. No. 5,782,740 describes a rapid exchange type intravascular catheter suitable for maintaining patency of a body lumen for a period of time sufficient to permit delivery of a radiation source to the body lumen. The catheter utilizes a reinforcing mandrel to improve the pushability and strength of the catheter as it tracks along a guide wire, and permits blood flow through an inflatable member while radiation therapy is being provided.

U.S. Pat. No. 5,816,999 describes the provision of ionizing radiation from an extracorporeal source to the interior of an internal body cavity or lumen and the dispersion of this radiation across a desired area of diseased tissue. It consists of an extracorporeal radiation source, a flexible catheter containing at least one hollow conduit for the transportation of the radiation along a curved path, an entrance portion to the catheter for the capture of the radiation, and an x-ray dispersive closure cap at the distal end of the catheter for the dispersion of the radiation within the body cavity or lumen and onto a specific area of tissue. It can be used to destroy cancerous regions within the body, such as in the pulmonary system, as well for applications in the vasculature and other internal regions of the living body.

U.S. Pat. No. 5,566,221 describes a kit for delivering x-rays to the interior surface of a body cavity. The kit includes an x-ray source and an x-ray source guidance tube. The guidance tube includes an inflatable inelastic balloon disposed about and affixed at its distal end such that when inflated, the central axis of the balloon is coaxial with and is disposed about the central axis of the tubular element Inflation and deflation of the balloon is controllable from the proximal end of the tubular element. The x-ray source may include an electron-activated target for generating x-rays in response to electrons incident on the target. The x-ray source may also include means for generating an electron beam and steering the beam so that it is incident on the target. The target end is slidably positionable within an interior channel of the source guidance tube.

U.S. Pat. No. 5,562,633 describes a catheter placement unit having an introducing needle having a pointed tip for introducing a catheter into a desired position in a patient's body, a needle hub for mounting the needle so that the needle extends through an axial bore in the catheter during introduction of the catheter into the patient's body and so that the needle can subsequently be withdrawn from the catheter bore leaving the catheter in position in the patient's body, and a needle tip protector on the needle for shielding the needle tip when the needle has been withdrawn from the catheter bore. The needle tip protector includes a guard element which is held against a resilient bias in a cocked position to one side of the catheter while the catheter is introduced into the patient's body and which, on subsequent withdrawal of the needle from the catheter bore, is moved laterally by resilient action from the cocked position into a guard position in which it shields the needle tip. Thus the protector reliably guards against needle stick injuries during withdrawal and subsequent disposal of the needle.

U.S. Pat. No. 5,041,107 describes an implantable apparatus for continuous or periodic introduction of a drug to a desired release point in the body comprises an implantable power source and an elongated flexible plastic tubular catheter having a lumen filled with the drug to be delivered and containing therein a first device electrode. The distal end of the catheter is closed and located near the distal end is a port which extends through the wall of the catheter to communicate with the lumen. Just proximal of the port is a surface electrode mounted on the exterior wall of the catheter body. Extending through the catheter and joined to the drive electrode and the surface electrode are conductors which couple those electrodes to the implanted power source. Energization of the electrodes with a predetermined direct current potential causes a flow of the ionized drug molecules out through the port and into the area surrounding the surface electrode.

U.S. Pat. No. 5,599,346 describes a radio frequency (RF) treatment system includes first and second catheters with first and second needle electrodes positioned at least partially in lumens of the first and second catheters. Each electrode is surround by a insulator sleeve which is slideable along the electrode and defines an ablation surface. An RF power source is coupled to the first and second needle electrodes. The electrodes provide bipolar RF ablation between the two, defining an ablation volume. A deflectable introducer has a laterally deflectable distal end and an ablation volume temperature sensor positioned at the distal end. The deflectable introducer is advanced in and out of the electrodes distal ends to measure a temperature of tissue in the ablation volume. The treatment system can include more than two electrodes, such as two pairs of electrodes. Further, the system can include a needle electrode extension with a laterally deflectable distal end. The needle electrode extension is positioned in at least one of the distal ends of one of the needle electrodes. It is advanced in and out of the needle electrode distal end to provide monopolar ablation. Additionally, the RF treatment system provides for the introduction of an infusion media, including but not limited to a chemotherapeutic agent, through distribution ports in the needle electrodes, or through one or more infusion devices that can house the needle electrodes and their respective catheters.

One problem with all of the foregoing devices is anchoring the device to the desired site within a subject, in part due to a high degree of relative motion in living systems between an endoscope and the target organ, this relative motion increases the likelihood of improper positioning without a suitable endoscope anchoring system. Improper positioning can lead to ineffective therapy and undesirable side effects. The present invention provides an anchoring system that overcomes the problems of prior art devices.

The present invention also allows the penetration of x-rays to kill lesions that are located behind the surface of healthy tissue regions in the body or lesions that are partially thick or massive. This is a significant advantage of targeted minimally invasive therapy compared to externally applied radiation technique. For example, gastrointestinal lesions often begin on the internal lining (endotheliem) of the organ. Accordingly, treatment of such lesions with externally applied x-rays requires the application of higher power over a broad volume of healthy tissue between the skin and the lesion. However, positioning the x-ray source at the lesion advantageously achieves the same or higher power density at the site of the lesion while lowering the overall x-ray energy dissipated in healthy tissue.

SUMMARY OF THE INVENTION

The present invention relates to an x-ray catheter having an anchoring system made of retractable needles which secure the x-ray catheter into position on the target tissue, and can be optionally used to inject drugs into the patient, and to measure the distance between the x-ray source and the tumor.

This invention preferably provides a removable attachment to an x-ray catheter that contains a x-ray source. The anchoring or positioning system is formed as a metal shield that shields emissions of x-rays from the x-ray source. A set of needles is retractably affixed to the shield. These needles are affixed on rows on opposite sides of the x-ray source. A sleeve is provided wherein that the needles may be retractably sheathed adjacent to the x-ray source. Each needle of the multiple needle assembly is pivotally attached to the shield by a pin that allows the needle to move between a retracted position and an activated position. In the retracted position the needles can be safely pushed into and out of the body, and a sleeve is preferably provided over the needles for safety.

In the activated position, the needles extend into a position such that they are facing in the same, general direction as the desired site of irradiation. Control connects between the needles and the control system outside the patient, wherein, by manipulation of the control, the needles extend into their anchor position. In an alternative embodiment, suction can be used to engage the needles into the tissue.

The endoscope positions the needle system while the needles are extended. The endoscope is then used to embed the needles into the region by applying force. An inflatable balloon system may also be used to press the device into the tissue. The needles may be solid or hollow with infeed and exit openings.

Optionally, a therapeutic or diagnostic agent may optionally be delivered from a reservoir that communicates with the needles through hollow tubing. In this embodiment, the needles are hollow, but they may be solid if delivery of a therapeutic agent is not required. The needle can also be coated with a therapeutic or a diagnostic agent. In some instances, the needles can be retracted and in others they can be left in place if "break away" needles are used. Addition of a score line on the needle at a proper position will break away when the proper force is applied.

The needles preferably have markings in them so that the vision system of the endoscope can determine the position and depth of the needles. This insures the proper x-ray dose and (b) can insure that therapeutic agents, when required, are delivered to the tumor region and not to healthy tissue.

In an alternative embodiment, the x-ray catheter include a housing having a suction opening and connected to a vacuum source, an x-ray catheter having an x-ray source therein and an x-ray transparent window adjacent the x-ray source. The x-ray catheter is placed inside the housing such that a space is formed therebetween, and the suction opening being in operative alignment with the x-ray transparent window such that x-ray may exit the window and the suction opening, the vacuum source crating suction at the suction opening to adhere the device to the desired site.

BRIEF DESCRIPTION OF THE FIGURES

FIG. 1 is an isometric view including the metal shield, the catheter and the window that allows the x-rays to be released, showing alignment of the needles and window.

FIG. 2 shows a cross-section showing the cylindrical case and its control wire, a tube system for the drug delivery system, and hinge and control mechanism and the x-ray window.

FIG. 3 shows the system in the folded position.

FIG. 4 shows a top down view of the device showing the successive positioning of needles. further away from the housing to allow each needle to move without interacting with each other.

DETAILED DESCRIPTION OF THE INVENTION

Figure 5:
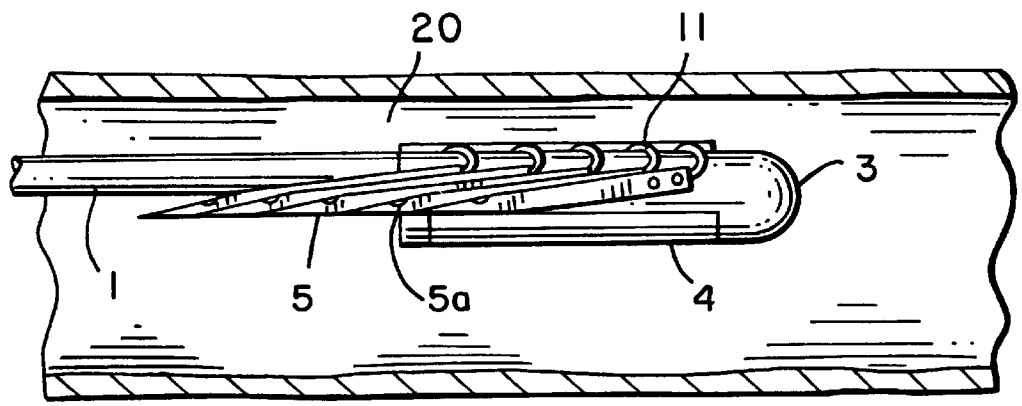
FIGS. 5, 6 and 7 show the positioning, opening and placement of the system and application of x-rays. This embodiment includes a balloon position system.

Referring to FIG. 1, x-ray catheter 1 having a metal shield 3 and x-ray source 2, which generally includes a vacuum tube housing electrodes operatively connected to a power source, is located at a distal end of the catheter. Metal shield 3 has x-ray transparent window 4 therein. X-ray transparent window 4 is made of a material transparent to x-rays so that they may pass through the device to the tissue site. Retractable needles 5 (shown in extended position) project outward from x-ray source without blocking the path thereof. Cavities may be provided in the sheath for the needles to retract therein.

Retractable needles 5 are made of metal or other suitable material, and can be solid or hollow to allow for, e.g., the delivery of a therapeutic substance. The needles may be made of surgical grade stainless steel, e.g., 304 grade, or may be made of a memory-type metal such as made of Nitinol™ so that allow the needles to maintain their shape. Preferably, the needles are etched or otherwise marked with indicators to allow the user to determine the depth of the needle in the tissue during the endoscopic procedure. The needles may also be scored to break and remain in the tissue and can serve as a marking or locating device for future procedures. Breakable needles can also be made of radioactive material, and may be inserted in to the tumor and separated from the device so that they can provide continuing low dose therapy.

The needles may be solid or hollow having entrance and exit ends for delivering therapeutic or diagnostic agents. Optionally, he needles may be coated on an outer surface thereof with a therapeutic or diagnostic agent.

FIG. 2 shows needles 5 in more detail. Retractable needles 5 may have openings 5a therethrough or be solid and are retractably attached to the device by pins 6. Fluid tubes 11 communicate with the needle core of the respective needle and with a reservoir (not shown) containing an active or therapeutic substance, which can be delivered therethrough to the affected tissue. Fluid tubes 11 are sufficiently flexible to allow retraction of the needles, Hinge 7 is operably connected to control 9 which extends to the distal portion of the endoscope and is manipulated by the user to extend or retract the needles. Control 9 is made of a metal wire having sufficient rigidity to extend and retract the needles into position.

Sheath 8 is operatively connected to a sheath control 10 and is retractable over the distal end of the device when the needles are retraced.

FIG. 3 shows needles 5 in retracted position inside the device. FIG. 4. is a view from the top of the device. The needles are spaced increasing distances from the wall of the shield so that they may conveniently fit inside the device.

Figure 6:
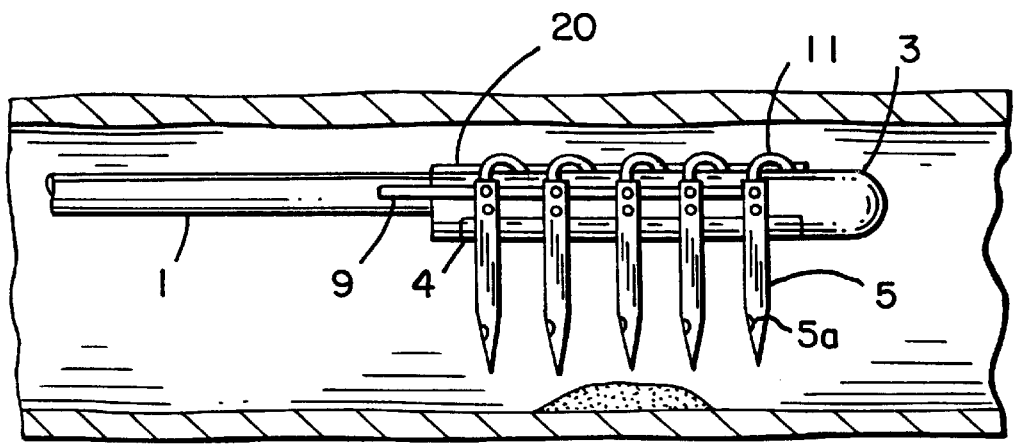
Figure 7:
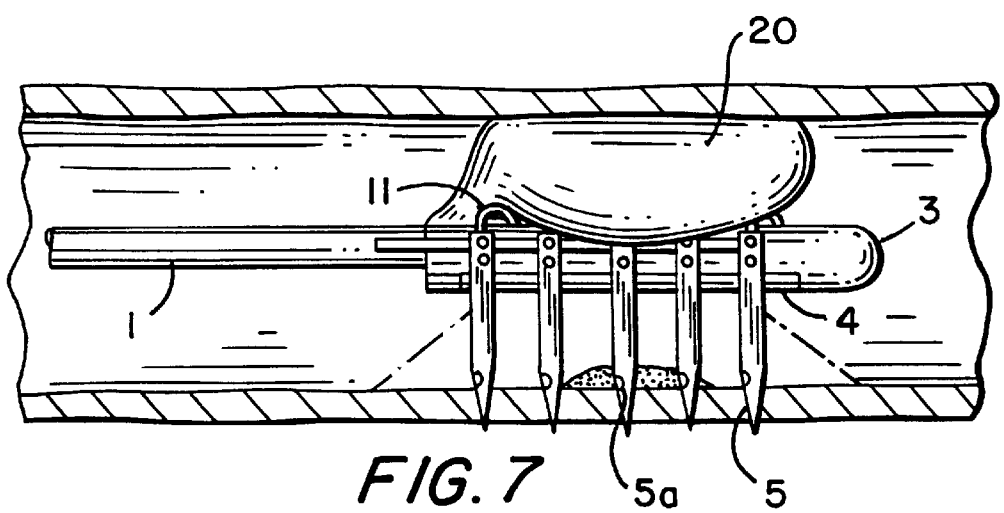

FIGS. 5, 6 and 7 detail operation of the device in a body lumen. The catheter 1 enters the body lumen With needles in retracted position. At the desired site, the operator manipulates the control 9 to extend needles 5 to extended position. In this embodiment, a balloon 20 is inflated to penetrate needles 5 into the target tissue. Balloon 20 communicates via ducts with a reservoir containing gas or liquid for inflation. Once property positioned, the site is irradiated with the therapeutic dose of material. The balloon or balloons may be affixed to the catheter with a suitable adhesive. The balloons may be contained in a hollowed portion of the catheter for storage.

Therapeutic agents or diagnostic aids may be delivered through the needles to the target tissue. Typically, local anesthetics or chemotherapeutic agents will be administered.

Figure 8:
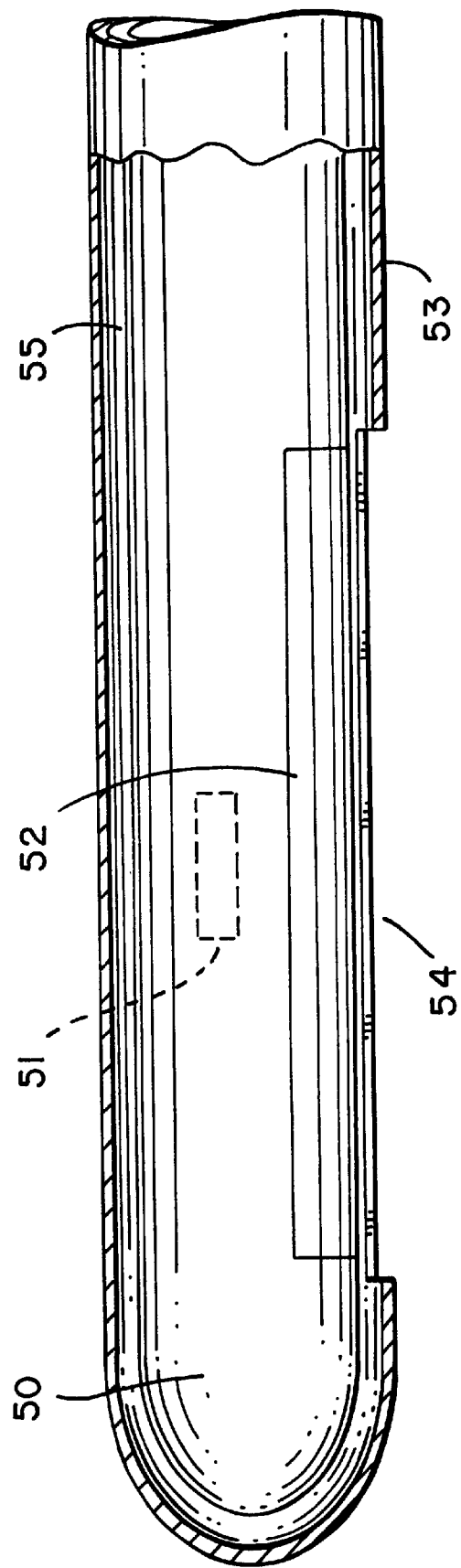
FIG. 8 shows an embodiment with a suction opening as a positioning system.

Another preferred embodiment elates to an x-ray device that uses suction rather that retractable needles to position the x-ray source at the desired site. As shown in FIG. 8, catheter 50 having x-ray source 51 disposed therein adjacent to x-ray transparent window 52 is disposed in a housing 53 having suction opening 54 therein. Suction opening 54 is in alignment with x-ray transparent window 54 and allows passage of x-rays from x-ray source 51 to the site. There is a vacuum space 55 between catheter 50 and housing 53, which is connected to a vacuum source to create suction at opening 54, allowing the x-ray source and catheter to adhere to the desired site, e.g., a tumor, without additional position means.

Other embodiments will be readily apparent to the skilled artisan without departing from the spirit or scope of the invention, which is limited only by the claims appended hereto.

It is claimed:

1. An x-ray catheter comprising:
   an x-ray tube having an x-ray source therein and an x-ray transparent window through which x-rays may pass; and
   a positioning device comprising retractable needles, said needles retractably attached to a hinge which is operatively connected to a control which extends or retracts said needles from the device, the needles positioned adjacent the x-ray transparent window so as not to impede the flow of x-rays.

2. The x-ray catheter of claim 1, wherein said needles are made of steel.

3. The x-ray catheter of claim 1, wherein at least one of said needles contains a therapeutic radioactive material.

4. The x-ray catheter of claim 1, wherein the non-pointed end of the needles communicate with a reservoir containing a therapeutic agent by a duct or tube.

5. The catheter of claim 1, wherein the needles are marked to identify the depth the needle has penetrated tissue.

6. The x-ray catheter of claim 1, further comprising an inflatable balloon or an outer surface thereof.

7. The x-ray catheter of claim 1, wherein the needles are coated with a diagnostic or therapeutic agent.

8. The x-ray catheter of claim 1, wherein the needles are scored and break way from the device upon sufficient force.

9. An x-ray catheter comprising;
   a housing having a suction opening and connected to a vacuum source an x-ray catheter having an x-ray source therein and an x-ray transparent window adjacent the x-ray source;
   the x-ray catheter being placed inside the housing such that a space is formed therebetween, the suction opening in operative alignment with the x-ray transparent window such that x-ray may exit the window and the opening, the vacuum source creating suction at the suction opening to position the device at the desired site.

* * * * *